Figure 1:
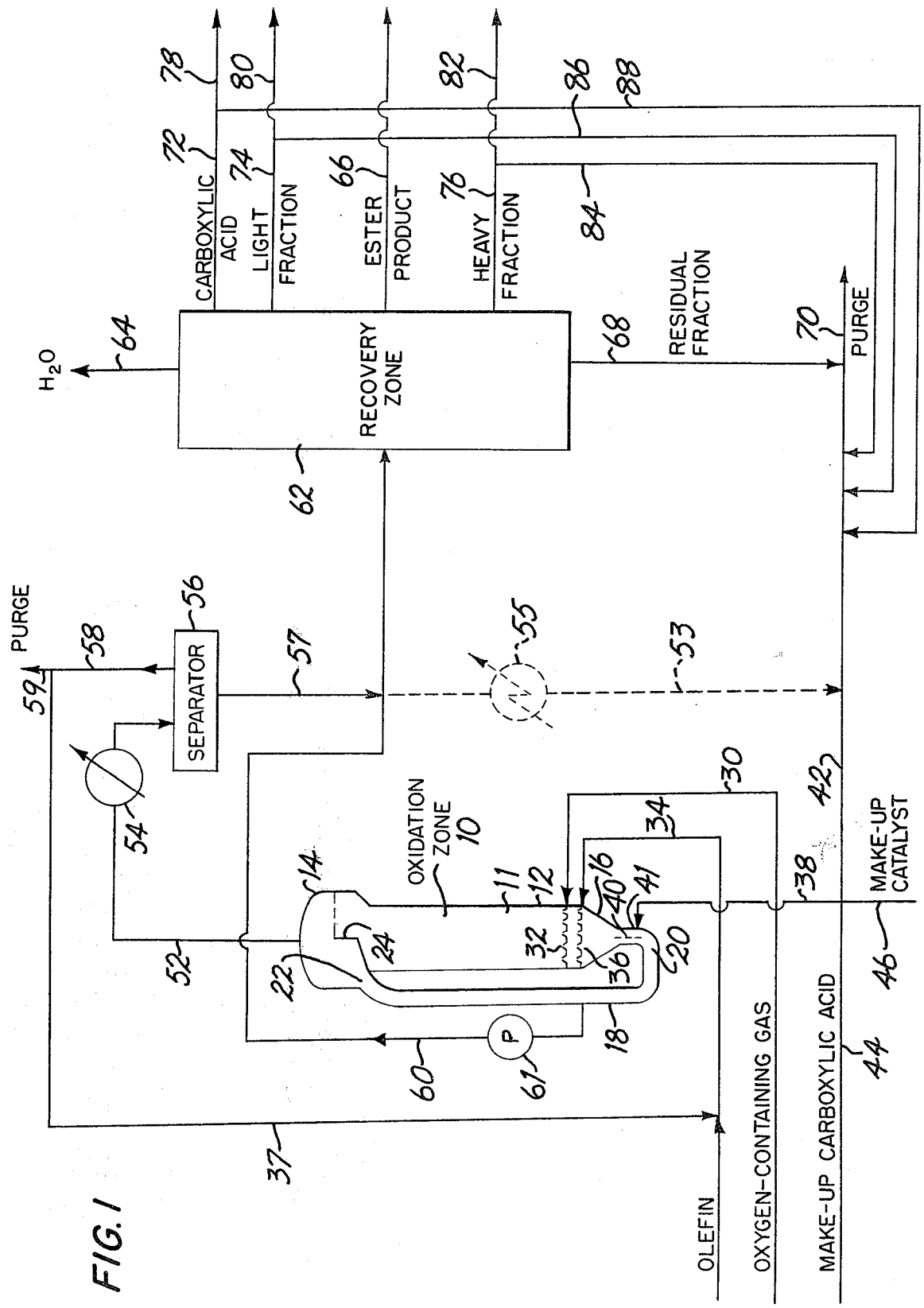

United States Patent [19]

Peltzman

[11] 4,245,114

[45] Jan. 13, 1981

[54] GLYCOL ESTER PREPARATION

[75] Inventor: Alan Peltzman, New York, N.Y.

[73] Assignee: Halcon Research and Development Corporation, New York, N.Y.

[21] Appl. No.: 971,133

[22] Filed: Dec. 19, 1978

Related U.S. Application Data

[63] Continuation-in-part of Ser. No. 753,139, Dec. 21, 1976, abandoned.

[51] Int. Cl.$^3$ ............................................. C07C 67/05
[52] U.S. Cl. .......................... 560/246; 260/465 D; 260/465.4; 560/20; 560/106; 560/112
[58] Field of Search ................. 560/246, 20, 106, 112; 260/465 D, 465.4

[56] References Cited

U.S. PATENT DOCUMENTS

| | | | |
|---|---|---|---|
| 3,346,624 | 10/1967 | Schaeffer | 560/246 |
| 3,493,609 | 2/1970 | Kronig | 560/246 |
| 3,715,389 | 2/1973 | Hoch | 560/246 |
| 3,872,164 | 3/1975 | Schmidt | 560/246 |
| 3,907,874 | 9/1975 | Harvey | 560/246 |
| 4,008,286 | 2/1977 | Hirose | 560/246 |

OTHER PUBLICATIONS

Groggins, "Unit Processes in Organic Synthesis," 3rd Ed., pp. 445–452 & 481–482 (1947).

*Primary Examiner*—Natalie Trousof
*Assistant Examiner*—Michael Shippon
*Attorney, Agent, or Firm*—William C. Long; David Dick; Riggs T. Stewart

[57] ABSTRACT

In the preparation of glycol esters by the liquid phase reaction of an olefin, molecular oxygen, and a carboxylic acid in the presence of a catalyst system comprising a variable valent cation in association with bromine, chlorine, a bromine-containing compound or a chlorine-containing compound, improved reaction rate and product selectively are achieved by carrying out the reaction in a vertical reaction zone communicating with at least one zone for movement of liquid from the top of the vertical reaction zone to the bottom of said reaction zone, and providing gaseous and liquid feeds in predetermined relationships and providing predetermined vertical superficial liquid velocities.

7 Claims, 3 Drawing Figures

GLYCOL ESTER PREPARATION

REFERENCES TO RELATED APPLICATION

This is a continuation-in-part of Ser. No. 753,139, filed Dec. 21, 1976 now abandoned.

This invention relates to the preparation of glycol esters and is more particularly concerned with an improved process for producing glycol esters in a catalytic reaction involving an olefin, a carboxylic acid and oxygen.

Glycol esters, and especially glycol carboxylic acid esters, are particularly useful organic chemical intermediates and extractive solvents. The glycol esters produced from ethylene are useful in the production of ethylene glycol, an important commercial chemical. Catalytic processes for the preparation of the glycol esters have been disclosed, for example, in U.S. Pat. No. 3,689,535 and in Belgian Pat. No. 738,463. Ethylene glycol may be prepared by the hydrolysis of the ethylene glycol carboxylic acid esters, as disclosed in U.S. Pat. No. 3,647,892, and vinyl acetate may be prepared by pyrolysis of the ethylene glycol ester, as disclosed in U.S. Pat. No. 3,689,535. Similarly, propylene glycol may be prepared by the hydrolysis of propylene glycol carboxylic acid esters, and other glycol esters yield the corresponding glycols upon suitable hydrolysis.

While the known processes for producing glycol esters, such as those disclosed in the above-mentioned patents, are effective for the indicated purposes, they are susceptible of improvement from the standpoint of optimum operation with respect to conversion, selectivity, and yield.

It is accordingly an object of the present invention to provide a process for the preparation of glycol esters wherein improvements can be realized in conversion, selectivity, and yield, and there can be attained significant operating and economic advantages.

It has now been discovered that the continuous reaction involving the olefin, oxygen and the carboxylic acid can be effected with desirable characteristics such as improved reaction rate, selectivity, economics, and the like by carrying out the reaction under predetermined flow conditions in a vertically-elongated reaction zone adapted to contain a body of liquid reaction mixture and provided with a branch vertical circulation zone for continuously transferring liquid from the upper portion of the body of the liquid reaction mixture to the lower portion of that liquid body.

Such vertical circulation combined with reactant introduction into the lower portion of the liquid reaction mixture under continuous conditions provides a means for predetermining the superficial liquid velocity through the reaction zone and for varying the partial pressure profile of molecular oxygen through the reaction zone. It is thus possible to provide a liquid superficial velocity which ensures a more uniform reaction zone temperature and allows for the effective suspension of particulate matter present in the reaction zone.

The continuous catalytic reaction involving the olefin, oxygen and the carboxylic acid includes redox reactions in which the zero valent element and its variable valent cation participate. High oxygen partial pressure minimizes the presence of the zero valent element. High superficial liquid velocities increase the extent of suspension of this elemental particulate which may be present. Furthermore, it has been found that reaction rate and selectivity are both directly related to the presence of variable valent cation dissolved in the reaction medium.

The superficial liquid velocity in a vertical reaction zone provided with top-to-bottom circulation in the manner proposed in connection with this invention is influenced by the length to diameter relationship of the reaction zone, the rate of total gas flow and the extent of forced circulation, if any. In accordance with the invention, the length to diameter relationship is at least 3:1 but generally is not greater than 40:1. The volume of liquid in the reaction zone is related to the length-diameter relationship and the values of each may be freely chosen as long as the minimum value mentioned above and the desired volume have been provided. The total gas rate, i.e., olefin, oxygen-containing gas and recycle gas, taken with the length-to-diameter relationship, serve to establish the degree of aeration of the system and therefore its driving force for natural circulation. The volume of natural circulation plus forced circulation (including liquid feed) divided by the cross-sectional area of the reaction zone equals the liquid superficial velocity. Thus, for a reaction zone of given dimensions, the degree of aeration can be varied by varying the quantity of recycle gas and thus the natural circulation can be influenced. The superficial velocity can be further controlled, if necessary, by varying the extent of forced liquid circulation. The portion of the superficial velocity attributable to forced liquid circulation is set only by the characteristics of the pumping means and the reaction zone cross-sectional area. This portion of the liquid superficial velocity is totally independent of reaction conditions. The liquid feed to the reaction can be considered a part of the forced circulation component. Hence, for any given length-diameter relationship originally set to provide a given unaerated liquid volume with a given minimum gas rate, it is possible to control the liquid superficial velocity by varying either the forced circulation component or by varying the natural circulation component by controlling the recycle gas rate, or both.

Thus, it has been discovered that the foregoing and other objects can be achieved by conducting the reaction in a reaction zone of the type indicated with superficial liquid velocity controlled and maintained in a specified range.

It has been observed that, when the catalytic liquid phase reaction of an olefin, molecular oxygen, and a carboxylic acid is carried out as described herein, meaningful improvements in selectivity, conversion and/or yields are reproducibly obtained and the reaction proceeds smoothly and uniformly.

The reaction system with which this invention is particularly concerned relates to the production of monobasic carboxylic esters of vicinal glycols by the oxidation with molecular oxygen of an olefin in the presence of a monobasic carboxylic acid, and in the presence of a catalyst system comprising a non-noble metal variable valent cation plus at least one of bromine, chlorine, a bromine-containing compound or a chlorine-containing compound. Such catalyst systems are disclosed, for example, in U.S. Pat. No. 3,689,535, U.S. Pat. No. 3,668,239, British Pat. No. 1,289,535, and said patents are incorporated herein by reference. The glycol moiety of the ester products of the process has a carbon structure corresponding to that of the olefin, while the acyl moiety of the ester products corresponds to that of the monobasic carboxylic acid. The following chemical equations illustrate the primary chemical reactions involved in the process of this invention (wherein ethylene is the olefin and acetic acid is the carboxylic acid), but there is no intent to limit this invention to the specific embodiment illustrated:

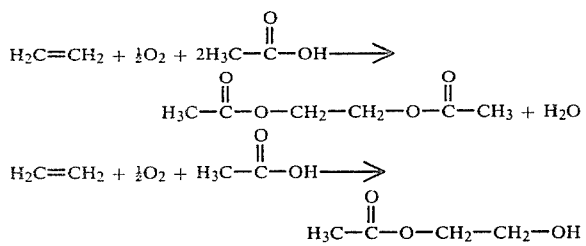

The liquid-phase reaction medium with which this invention is concerned and which is present in the oxidation zone contains the carboxylic acid, the glycol ester products of the reaction, precursors of the desired glycol ester products of the reaction, reaction by-products, including water and halogenated reaction by-products, as well as the catalyst system employed, dissolved olefin and dissolved oxygen also being present. Normally, the liquid reaction medium will contain from 5 to 60 mol percent of the carboxylic acid, and 5 to 60 mol percent of the reaction products including glycol dicarboxylate, glycol monocarboxylate, precursors of the desired esters and by-products. Such precursors include the glycol corresponding to the olefin itself, higher-boiling materials, ether alcohols, as well as halogenated precursors, the halogen being introduced into the system as a catalyst component. For example, when the olefin is ethylene, the carboxylic acid is acetic acid, and bromine or a bromine-containing compound is employed, such higher-boiling materials include di-ethylene glycol, tri-ethylene glycol and their mono- and di-acetate derivatives, and the halogenated precursors include ethylene bromohydrin, 2-bromoethyl acetate, 1,2-dibromoethane and brominated derivatives of the higher-boiling materials. The principal by-product is water. The catalyst system will generally be present in the amount of 0.1 percent to 30 percent by weight. The reaction is carried out continuously with a portion of the liquid phase reaction medium being continuously withdrawn from the oxidation zone and processed to recover reaction products, unconverted reactants, and by-products, some of which are recycled to the oxidation zone as will be hereinafter discussed. At the same time, olefin, carboxylic acid, and oxygen, together with recycle components are continuously introduced into the reaction zone. The liquid feed suitably contains the catalyst components dissolved or suspended in it.

In Hoch et al U.S. Pat. No. 3,715,389, the disclosure of which is incorporated herein by reference, it is pointed out that the maintenance of an oxygen partial pressure within specified limits is important in achieving desirable reaction rates, especially in a continuous system with recycling of the gaseous components of the system. It has now been discovered that maintenance of these desired reaction rates provided by the control of oxygen partial pressure can be ensured by carrying out the reaction with circulation of the liquid phase reaction mixture at predetermined rates. In a system of the character contemplated, the variable valent cation component of the catalyst system will exist partly in a solubilized form and partly in a non-solubilized form, the latter taking the form of relatively small particles which exist as a suspension in the liquid medium. It has now been discovered that improved reaction rates and product selectivity can be obtained by providing liquid phase reaction mixture recirculation which permits operation with maximum variable valent cation component of the catalyst system present in the reaction mixture in soluble form.

The operation of the oxidation reaction to achieve the desired conditions of maximum rate and selectivity is most readily carried out in an oxidation zone arrangement in which the vessel defining the vertically-elongated oxidation zone is provided with means defining a path or paths for vertical liquid circulation connecting the upper portion of the zone with the lower portion of the zone. This process liquid recirculation can be accomplished either by natural guided circulation or by positive pressure movement or by a combination of the two. The natural liquid circulation portion can be provided for internally by means of a downcomer or draft tube inside the vertical oxidation vessel, or it may be provided for externally by means of a downcomer leading to an external natural circulation line. The process liquid recirculation due to positive pressure movement (i.e. forced liquid recirculation) can be provided for externally, by means of a pump-around loop, i.e., a line containing a positive pumping means.

Invariably, the natural liquid recirculation component of the total process liquid recirculation will be taken at the liquid level in the reaction zone. Therefore, there will always be required one upper inlet to the liquid circulation path which is at the liquid level in the reaction zone. The forced liquid recirculation portion of the total process liquid recirculation (i.e. that due to positive pressure movement) can be drawn from any reaction zone location. That is, the feed to the external pump-around loop can be removed from the vertical reaction zone either at the liquid level where the natural recirculation component is taken, or at any other convenient location along the vertical dimension of the reactor. hence, the entire liquid recirculation can be provided for by a combination of both internal and external circulation and with either one or more paths thereby provided for connecting the upper portion of the reaction zone with the lower portion of the zone. An external path for at least a portion of this process liquid recirculation has the advantage that it can also serve to remove the heat generated by the reaction and, therefore, provides an effective means for temperature control.

The recirculating or recycle gas and the fresh molecular oxygen-containing gas are introduced into the oxidation zone separately. The feed of recycle gas takes place at a point near the bottom of the reaction zone but above the inlet of the recirculating liquid and it is preferably introduced at different points across the cross-section of the oxidation zone, e.g., through a sparger. The olefin is suitably combined with the recycle gas externally of the reaction zone so that a mixture of olefin and recycle gas is introduced. The molecular oxygen-containing gas may be wholly introduced by means of a sparger at the bottom of the oxidation reaction zone and above the region of introduction of the recycle gas, the sparger ensuring distribution of the oxygen to different points across the cross-section of the vertical reaction zone. Alternatively, the molecular oxygen-containing gas can be introduced in more than one portion into the vertically-elongated oxidation zone. These portions can be fed into the vertical reaction zone along its length above the point of introduction of the recycle gas at regular intervals. In all embodiments, however, the molecular oxygen-containing gas is introduced into the vertically-elongated oxidation zone above the point of introduction of recycle gas. The recycle gas is always introduced above the point of return of the recirculating process liquid. At the same time, the fresh liquid feed to this system which contains carboxylic acid recovered downstream of the oxidation zone, and other recirculating process moieties, e.g., glycol carboxylic acid esters, water, etc., this mixture also containing the desired catalyst quantity together with additional externally recycled liquid reaction mixture, can be introduced either at the bottom of the reaction zone or substantially axially in portions along the vertical dimension of the oxidation zone by means of spargers at axially spaced-apart locations. The number of such additions may be as many as desired to facilitate uniform reactor process liquid temperature.

In this manner, the process reaction liquid is back-mixed to a significant extent while the molecular oxygen content of the gaseous phase present in the reaction zone is kept in plug flow. That is, the concentration of the various components in the liquid phase present inside the vertically-elongated oxidation zone is maintained essentially uniform axially and radially throughout while the molecular oxygen content of the gaseous phase present in admixture with said liquid is essentially in plug flow. Furthermore, the back-mixed liquid has a large and controlled velocity component in the vertical direction which is effective in suspending and resuspending any variable valent cation which appears in elemental form during its path up through the reaction zone. The high partial pressure of molecular oxygen in the gas phase present in the lower regions of the vertical reaction zone just above the point of return of recirculating liquid serves to re-oxidize the elemental cation rapidly, thereby increasing the amount of active catalyst present in the liquid phase. Obviously, there is a practical maximum velocity but this is ordinarily determined by economic considerations and apparatus limitations, rather than by requirements of the reaction. As a general rule, however, vertical liquid medium superficial velocities are at least 0.05 ft/sec., preferably 0.1 to 1.5 ft./sec., most preferably at least 1 ft./sec., but velocities greater than about 2 ft./sec. serve no useful purpose in maximizing the reaction rate and product selectivity obtainable in the reaction zone.

The molecular oxygen-containing gas can be supplied in concentrated form, i.e., having an oxygen content of 85 mol percent or more, or it can be supplied in the form of air or in the form or enriched air or diluted air. The oxygen-containing gas and the olefin need not be specially purified and can contain those impurities normally associated with them. For example, the olefin can contain normal quantities, e.g., in the case of ethylene, up to 10 mol percent of ethane, or propane in the case of propylene, and the oxygen can contain nitrogen, argon, and like inert gases.

The olefins useful in the process of the invention are the mono-alkenes, cyclomonoalkenes, and aralkenes which can also contain functional substituents which are inert to the reaction such as nitro, cyano, halo (i.e, fluoro, chloro, bromo and iodo), lower alkoxy (methoxy, ethoxy, propoxy), lower alkylthio (methylthio, propylthio), hydroxy, lower alkanoyloxy of 1-3 carbon atoms (e.g., acetoxyloxy) and the like.

Particularly suitable mono-alkenes are the straight or branch-chain hydrocarbons containing from 2 to 6 carbon atoms. The double bond in the alkene can be positioned at any one of the carbon atoms such as the alpha, beta, gamma and delta positions and the like. Thus, such olefinic reactants include lower alkenes of from 2 to 6 carbon atoms such as ethylene, propylene, butene-1, butene-2, 2-methyl-butene-2, pentene-1, and the like.

Suitable aralkene reactants are those having an aromatic nucleus (i.e., the phenyl nucleus) and an alkenyl side chain co-extensive in scope with the alkenes as described above (i.e., with a $C_2$–$C_6$ unsaturated chain) attached to the phenyl nucleus. In addition to the alkenyl side chain, the nucleus can also contain one or two lower alkyl ($C_1$–$C_5$) substituents. For example, suitable aralkene reactants include styrene, alpha-methyl styrene, p-methylstyrene, and 3,5-diethylstyrene.

The cyclomonoalkenes of this invention are compounds containing from 4 to 12 nuclear carbon atoms and one double bond including, for example, materials such as cyclobutene, cyclopentene, cyclohexene, cyclodecene, and cyclododecene.

The carboxylic acid employed in the oxidation supplies the acyl moiety to the glycol ester and is preferably a lower aliphatic monobasic acid of from 1 to 6 carbon atoms such as formic acid, acetic acid, propionic acid, butyric acid, isobutyric acid and the valeric and caproic acids. Benzoic acid and its ring-substituted derivatives can also be used. For example, aside from benzoic acid itself, o-toluic, m-toluic, o-chlorobenzoic, m-chlorobenzoic, p-chlorobenzoic (or the brominated analogues of these materials), o-nitrobenzoic, m-nitrobenzoic, or p-hydroxybenzoic acids can also be used. Formic acid, acetic acid and benzoic acid are preferred species, and acetic acid is especially preferred.

The invention also contemplates the use of mixed carboxylic acid reactants in any desired ratio, although it is preferred to employ a single acid reactant when one wishes to avoid obtaining mixed ester products. The carboxylic acid can be employed in any commercially available form including the use of aqueous solutions thereof. It is preferred, however, to employ commercial acids having no more than 25% water, and especially less than 15% water, such as 90–98% acetic acid, or glacial acetic acid. The acids used can suitably contain the various organic and inorganic impurities normally associated with the various commercially available materials and, for purposes of this invention, such impurities can be allowed to remain or can be removed as one desires.

Correspondingly, the preferred glycol esters to the production of which the process of this invention is applicable include ethylene glycol diacetate, 1,2-propylene glycol diacetate, the corresponding diformates and dibenzoates, as well as the corresponding mono-esters.

The oxidation reaction with which this invention is concerned employs a catalyst system, such as disclosed in the above-mentioned U.S. Pat. Nos. 3,668,239 and 3,689,535 and British Pat. No. 1,289,535, which comprises a variable valent cation plus at least one of bromine, chlorine, a bromine-containing compound or a chlorine-containing compound. The variable valent cation can be utilized in its elemental form and added to the oxidation zone as a fine powder or can be added in any form which, in solution or suspension under oxidation conditions, will yield at least some soluble ions. For example, the cation source can be the carbonate, oxide, hydroxide, bromide, chloride, lower ($C_1$–$C_3$) alkoxide (e.g., the methoxide), phenoxide or carboxylate, e.g., acetate. In a preferred aspect, the cation is added as the oxide, hydroxide, carboxylate or halide. Furthermore, the catalyst compound employed can contain impurities naturally associated with the commercially available compounds, and need not be purified any further.

The preferred systems employ at least one of tellurium, cerium, antimony, manganese, vanadium, gallium, arsenic, cobalt, copper, selenium, or silver as the variable valent cations when using bromine or a bromine-containing compound, with tellurium, cerium, antimony, manganese or vanadium being the more desirable and tellurium, cerium, antimony, and manganese being most preferred. For use with chlorine or a chlorine-containing compound, the preferred catalyst contains cerium, manganese, arsenic, cobalt, copper, selenium or chromium; the more preferred being cerium, manganese, cobalt, copper and selenium, with the most preferred being cerium, manganese and cobalt.

When it is desired to use a bromine or a chlorine-containing compound in the reaction instead of bromine or chlorine itself, one can employ any compound capable upon oxidation of producing bromide or chloride ions in solution. For example, one can use hydrohalic acids (gaseous or aqueous, preferably concentrated aqueous acid), any metal halide such as the alkali, alkaline earth or heavy metal bromides or chlorides, (potassium bromide, calcium chloride, manganese bromide, lithium bromide and the like) the metal bromides or chlorides corresponding to the variable valent cations or organo-chlorine and organo-bromine compounds such as alkyl di-halides, lower aliphatic ($C_1$–$C_6$) halides (propylhalide, pentylhalide), cyclo lower aliphatic halides (cyclohexylhalide) or lower aliphatic dihalides, (ethylene dichloride, dibromoethylene) and all of the halogen-containing diester precursors, all of which are considered for nomenclature purposes to be compounds capable of producing bromide or chloride anions. Also contemplated is the use of a mixture of two or more halogen-producing compounds, containing the same or different halogen, as well as mixtures wherein the cation of the halide compound can be the same or different from the cation of the other compound employed. The halogen employed may suitably contain impurities normally associated with the commercially available halogen and in the preferred aspect of this invention the commercially available materials are employed.

Of all the catalyst systems, that most preferably employed is one comprising a tellurium cation (supplied to the oxidation zone in the powdered elemental form, the oxide, the carbonate, or in any one or more of the forms referred to above, but most preferably as the oxide) in conjunction with a bromine source.

The various reactants employed in the oxidation reaction can be effectively used over a wide range of concentrations. Catalyst concentrations can also vary widely, depending upon temperature, residence time and the type of halogen. Effective amounts of catalyst, expressed in weight percent of bromide or chloride to total liquid phase reaction medium, can be from 0.01% to 30% or higher, but preferably from 0.1% to about 20% and especially from about 0.5% to about 10%. The concentration of total operable variable valent cation present, expressed in terms of equivalents of cation-/equivalents of halogen expressed as bromine or chlorine, can vary from about 1:0.01 to about 1:1000 but preferably from about 1:0.2 to about 1:40, and especially from about 1:1 to about 1:20.

The mol ratio of oxygen to olefin in the feed is not critical and, therefore, any suitable mol ratio such as 1:1000 to 1:0.01 may be used, provided, of course, that the mixture is not in the explosive region. The source of the oxygen can be high-purity oxygen, or a mixture of oxygen and an inert gas such as found in air, or it can, in fact, be air.

The temperatures maintained in the oxidation zone can vary from about 50° C. to the bubble point of the liquid phase reaction mixture within the zone but generally will be between about 50° C. and about 200° C., desirably between about 90° C. to about 180° C.

Any pressure sufficient to maintain a liquid phase within the oxidation zone can be employed. Generally pressures from about atmospheric or below to about 1000 psia and preferably from about 25 psia to about 1000 psia would be used. Preferably, however, for the oxidation of lower olefins such as ethylene and propylene, the total pressure of the oxidation zone should be maintained at from about 50 to 1000 psia, and most preferably about 200 to about 500 psia. For the higher olefins, the pressure can be from about 25 to about 500 psia.

The time of reaction depends to a great extent upon the concentration of reactants and, therefore, may suitably vary over a wide range. Flow rates are preferably adjusted so that the rate of formation of product, as glycol diester, is from about 0.10 to 10 grams-mols per liter of liquid phase reaction medium per hour. Once steady-state conditions are obtained, the reaction can be continued with from about 5 to about 60% by weight of glycol ester products remaining in the liquid phase reaction medium, but this concentration is preferably maintained at from about 15 to about 50% by weight, based on the total weight of the liquid.

If desired, the reaction can be carried out in the presence of an inert solvent. Examples of such inert solvents are aromatic hydrocarbons, alkanols and esters, e.g., benzene, t-butanol, ethylene glycol diacetates, and the like. Preferably, however, the carboxylic acid reactant necessarily present in the liquid-phase reaction medium is used not only as the source of the acid moiety of the desired ester, but as a solvent as well.

The invention will be more readily understood by reference to the accompanying drawing, wherein, FIG. 1 is a schematic representation of an illustrative system which can be employed in carrying out the process of this invention, including an apparatus arrangement which is one of many that has been found to be particularly effective for providing the desired continuous oxidation which maximizes the attainable reaction rate and selectivity.

Figure 2:
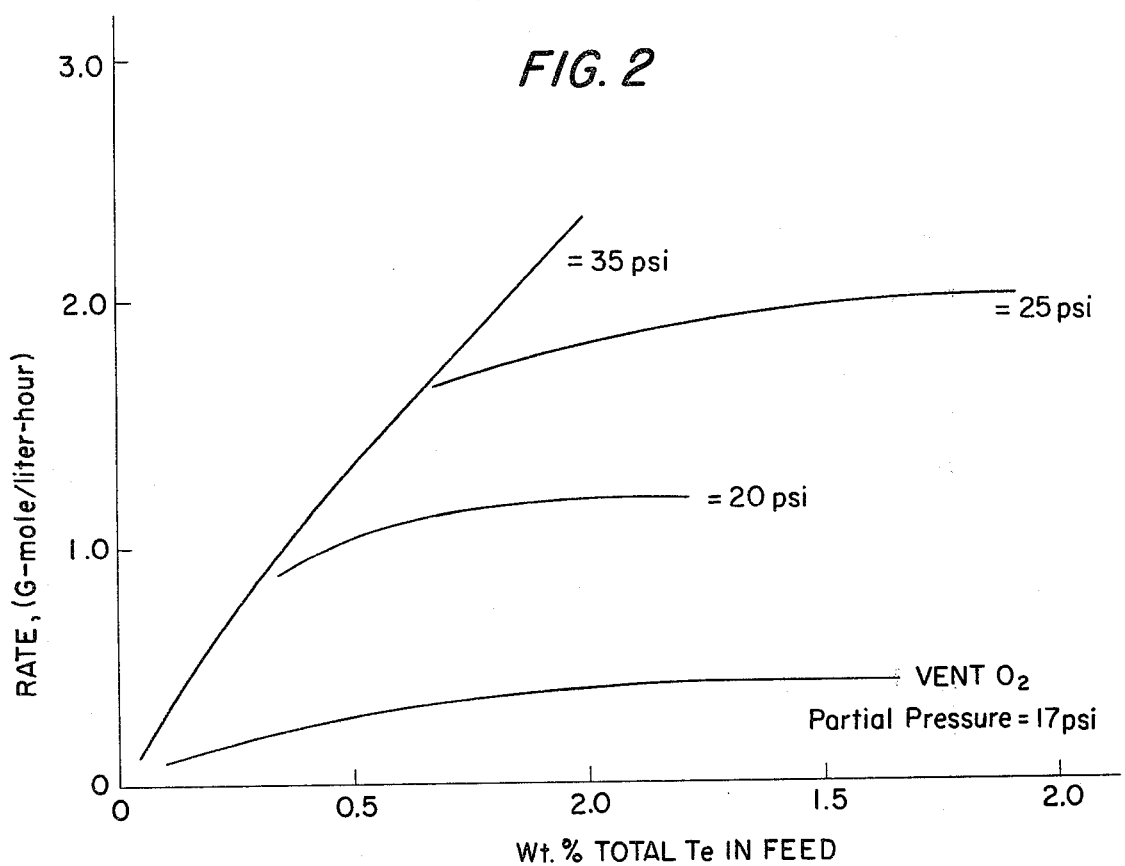
Figure 3:
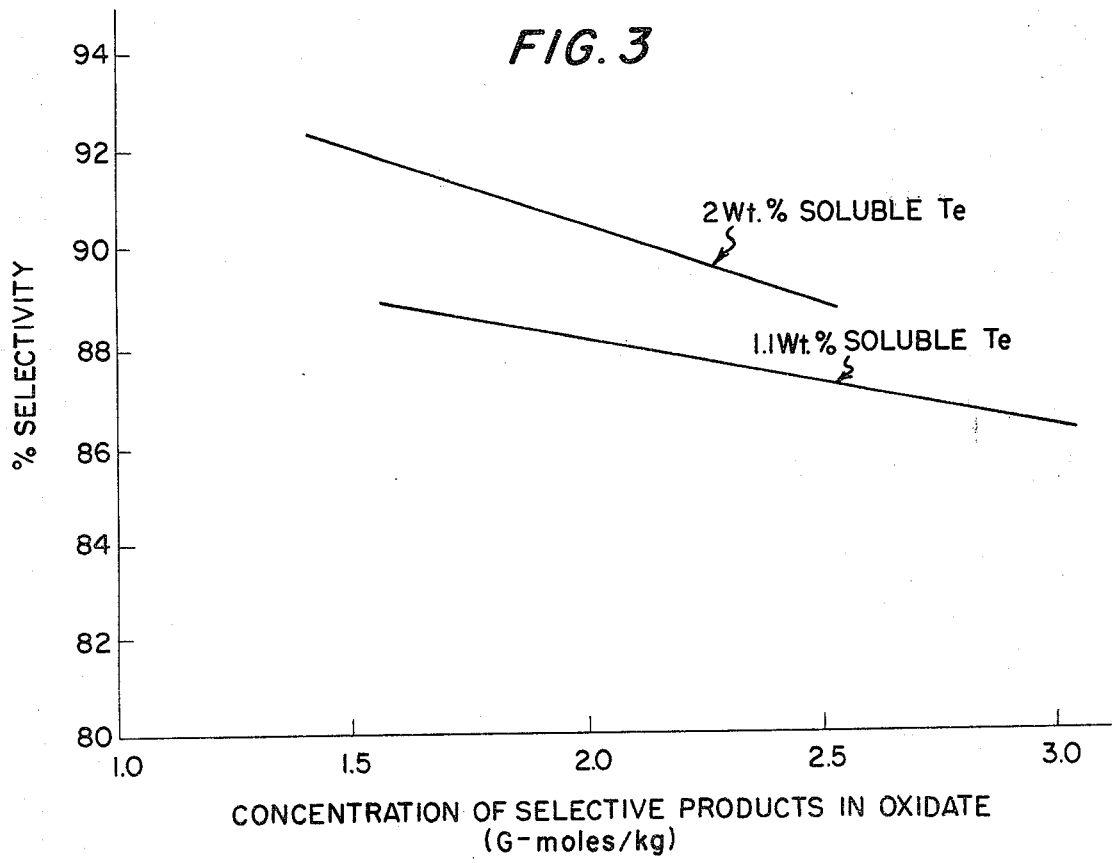

FIG. 2 is a graphic representation of the effect of oxygen partial pressure on reaction rate under different concentrations of catalyst, and FIG. 3 is a graphic representation of the effect of soluble catalyst on selectivity.

The description of the drawing which follows will serve to provide a fuller understanding and explanation of the invention and its advantages.

In the following discussion the reactants are ethylene, acetic acid and oxygen, while the catalyst system is assumed to be cationic tellurium and anionic bromine, the latter being conveniently supplied as hydrogen bromide dissolved in acetic acid. Continuous operation is assumed. Referring to FIG. 1 the oxidation zone 10, within which is maintained a body of liquid-phase reaction medium 11, is defined by a vessel of generally circular cross-section having side walls 12, an upper head portion 14, and a lower inlet portion 16 which, in the embodiment illustrated, has an inverted, generally-conical configuration. A circulating arm 18 communicates with the inlet 16 and with the upper end of zone 10 at outlet 22. An internal overflow baffle 24 directs fluid from the upper surface of reaction medium body 11, into the arm 18 and determines the liquid level of body 11 in the oxidation zone 10. The oxygen-containing gas is introduced through line 30 which communicates with the lower portion of oxidation zone 10 and feeds into distributing means disposed internally of zone 10, suitably in the form of sparger 32. In like manner, the olefin, e.g., ethylene, is introduced through line 34, which also communicates with the lower portion of zone 10 and in like manner communicates with a distribution device suitably in the form of sparger 36. The recycle vapor stream in line 37 is mixed with the olefin stream in line 34. Liquid feed is introduced through line 38, which is illustrated as communicating at its end with an inlet line 40 disposed substantially axially through inlet throat 41.

The liquid feed includes a recycle liquid stream to be described below, which is supplied through line 42. Combined with the recycle liquid stream are make-up acetic acid (via conduit 44) and make-up catalyst (e.g., tellurium oxide and HBr dissolved in acetic acid) through line 46. As shown, the make-up acetic acid and catalyst are added to this stream before it enters the oxidation zone.

The drawing indicates separate introduction of ethylene and oxygen with the recycled vapor being combined with the ethylene. Alternatively, the recycled vapor can also be introduced separately. Normally, however, the recycled vapor and ethylene make-up are pre-mixed prior to entering the oxidation zone. Although these alternatives may permit one to operate in a manner such that the total oxidation zone gaseous feeds could be so rich in oxygen as to be within the flammable region were they fully pre-mixed, the rate of the reaction can be sufficiently high to permit safe operation even under such circumstances within the system, i.e., the oxygen reacts so quickly that the operation remains a safe one.

Vapor comprising unreacted ethylene and oxygen together with gaseous by-products and diluents and more volatile components of the liquid phase reaction medium is withdrawn from oxidation zone 10 via conduit 52 and partially condensed in cooler 54. Condensed liquid and uncondensed vapor are separated from each other in separator 56. As shown, the condensed liquid is withdrawn through line 57 which feeds into line 60. Heat of reaction can, if desired, be removed by various means including coils (not shown). The uncondensed vapor is withdrawn from separator 56 through line 58 and a small quantity of this vapor may be purged via line 59 in conventional manner. The balance of the vapor is the recycled vapor stream returned to oxidation zone 10 via line 37.

A portion of the liquid phase reaction medium is continuously withdrawn from the oxidation zone via conduit 60 which communicates with circulating arm 18 and is fed to recovery zone 62 by pump 61. A branch line 53 provided with a cooler 55 may be used to recycle by forced circulation selected portions of the liquid in line 60, as desired. Recovery zone 62 is depicted schematically, but it normally comprises a series of distillation columns of conventional type and design, and which form no part of the present invention. Other low and high-boiling by-products are also recovered within recovery zone 62 and may be used as such or recycled as desired. Within recovery zone 62 are separated the desired diester product (ethylene glycol diacetate), low-boiling by-products and high-boiling by-products, which include components of the catalyst system. Within recovery zone 62 by-product water and carbon dioxide are also removed as separate components or conjointly, e.g., through line 64. The carbon dioxide by-product can, if desired, be returned to the oxidation system to facilitate control of the recycled vapor composition. This would normally require additional facilities (e.g., compression equipment, not shown). Alternatively, of course, carbon dioxide by-product can be discarded. The diester product is withdrawn from recovery zone 62, e.g., through line 66, and can be used as such, for example, as a solvent or plasticizer, or can be subjected to further processing such as, for example, hydrolysis to yield ethylene glycol or pyrolysis to yield vinyl acetate, for example, as described in Kollar U.S. Pat. No. 3,689,535.

The non-vaporized portion of the reaction mixture, which includes non-volatile catalyst components and by-products and co-products of higher molecular weight is shown as being withdrawn through line 68 as a residual fraction which forms part of the recycle stream being returned to the oxidation zone through line 42. Purging of this residual fraction can be effected through line 70 as required in accordance with conventional practice. Thus, as shown in the drawing, the separation of the reaction product mixture is suitably carried out to provide a carboxylic acid fraction which is removed through line 72, a light fraction of components having boiling points above that of acetic acid but below those of components of the ester product, and a heavy fraction of materials having higher boiling points than the product esters but more readily vaporizable than the components of the residual fraction. The light fraction is suitably withdrawn through line 74 and the heavy fraction through line 76. Portions of each of these streams can be withdrawn from the system as shown in the drawing via lines 78, 80 and 82 and the remaining portion, or the entire amount removed from the recovery zone, can be combined with the recycle stream in line 42 for return to the oxidation zone 10, as desired, lines 84, 86 and 88 being provided for this purpose.

In any case, the recycle stream in line 42 is combined with the required amounts of make-up acetic acid and make-up catalyst and introduced into zone 10 through line 38 and through line 40 where it is combined with the recirculating liquid entering throat 20 from arm 18. In this manner the liquid phase is well mixed whereas the gas phase proceeds through the reaction zone 10 essentially in plug flow with regard to its molecular oxygen concentration. This maximizes the attainable rate and selectivity in accordance with the invention.

The following examples will serve to illustrate this invention further but are not intended to limit the scope thereof. Unless otherwise indicated, all parts and percents are on a molar basis.

EXAMPLE 1

Apparatus essentially corresponding to that depicted in the drawing comprising a 5.7-liter jacketed titanium-lined oxidizer having a height to average diameter ratio of about 30, with an overflow liquid circulating arm having an inlet at a point sufficient to maintain a 4.9 liter aerated liquid volume within the oxidizer is employed.

A withdrawal line for continuously removing a portion of the reaction mixture communicates about 30 cm. above the reactor bottom. The oxidizer is initially filled to the overflow point with a slurry of tellurium dioxide and hydrogen bromide dissolved in acetic acid and other brominated species, collectively referred to as "halogenated lights" having boiling points lower than that of the ethylene glycol esters which are also recycled to the oxidizer in admixture with the acetic acid. Overall, the slurry contains about 2 wt. % of tellurium as the dioxide and 8% of the bromide as HBr. The oxidizer is then heated under nitrogen to about 160° C. and ethylene and oxygen feeds are commenced (mol ratio of oxygen to ethylene is about 1:2). The oxygen employed is of 99.5% (mol) purity containing about 0.5% (mol) argon. Pressure is maintained at 28 atmospheres absolute by regulating the rate of gas withdrawal from the oxidizer. Gas withdrawn is compressed and recycled for admixture with the fresh gaseous reactants supplied, while a portion is purged to prevent uncontrolled build-up of diluents, e.g., argon. The purged material is first cooled to about 40° C. to recover the acetic acid contained therein. This acetic acid is recycled to the autoclave. The oxygen-containing gas and the ethylene are separately introduced into the bottom of the reaction zone and the recycle gas is combined with the ethylene prior to introduction into the reaction zone. The oxygen-containing gas stream is supplied at the rate of about 140 standard liters/hour (SLH) and the olefin-recycle gas stream enters at the rate of about 6350 SLH. At the same time, the liquid feed which is composed primarily of acetic acid containing catalyst is introduced at the rate of about 5.5 Kg/hr. The combined effect is the provision of an upward superficial liquid velocity in the reaction zone of about 1 ft./sec.

Liquid phase reaction medium is directed into the circulating arm as it builds up to the over-flow line and circulates at the rate of about 4 ft./sec. A portion of the reaction medium is continuously withdrawn and distilled (a) to eliminate water and carbon oxides together with minor amounts of other low-boiling materials from the system (b) to recover unconverted acetic acid for recycle to the oxidizer as a component of the liquid feed and (c) halogenated precursors (primarily 1-acetoxy-2-bromoethane but also containing some bromohydrin and other brominated species, collectively referred to as "halogenated lights") having boiling points lower than that of the ethylene glycol esters, which are also recycled to the oxidizer in admixture with the acetic acid. Glycol esters are recovered and all materials, brominated or otherwise, having boiling points greater than 1,2-diacetoxy ethane, including catalyst components are recycled to the oxidizer. Make-up acetic acid is supplied, initially in the form of the slurry described above (to prevent depletion of catalyst components as liquid phase is withdrawn) and then as glacial acetic acid, at a rate sufficient to maintain a constant draw-off rate of liquid phase reaction medium. The withdrawal corresponds roughly to a three-quarter hour residence time.

After about 10 hours of continuous operation in the manner described above, during which samples are periodically taken and analyzed to ascertain composition, steady state operation is achieved. Generally, the operation is maintained at steady state for a minimum of about 8 hours. Although provision exists for catalyst purge, over the duration of any one experiment, no such purge is required.

Analysis indicates that the selectivity to glycol moieties, i.e., glycol, glycol esters and their precursors obtained according to the foregoing procedure is about 94%, i.e., 94% of the ethylene reacted is in the form of glycol, glycol esters and precursors, while the rate of product formation is about 1.9 gram-mol/liter-hour. The foregoing experimental procedure is repeated except that the rate of introduction of the gas streams is reduced to a total rate of about 2750 SLH and the liquid superficial velocity in the reaction zone is about 0.7 ft./sec. Under these conditions, the rate of product formation becomes 1.6 gram-mol/liter-hour and the selectivity to glycol moieties is about 91%.

The foregoing experimental procedure was repeated a large number of times in order to study the effects of tellurium cation concentration and oxygen partial pressure on the rate of oxidation reaction and the selectivity to glycol moieties. The rates of introduction of the gas streams and the liquid streams were varied over a range wide enough to explore a representative regime of these variables.

The total gas rate was varied from about 900 SLH to about 12,000 SLH. The liquid feed rate was varied over the range of 1 Kg/hr. up to about 12 Kg/hr. The concomitant range of liquid superficial velocity which was studied varied from a low value of about 0.05 up to a value of about 2 ft./sec.

Attempts to operate at liquid superficial velocities of less than 0.05 ft./sec. resulted in uneconomic rates and selectivity to useful products.

FIGS. 2 and 3 attached summarize the results of these studies. It is seen that at a given total tellurium concentration in the reactor feed, increasing oxygen partial pressure results in significant increase in reaction rate. This comes about because the level of dissolved tellurium in the reactor rather than suspended elemental particulates increases with increasing oxygen partial pressure. The reaction process of the present invention permits this phenomenon to occur. Merely operating at very high total tellurium in the feed is insufficient. FIG. 2 teaches that the reaction vessel of the present invention permits the oxidation reaction to take place with a substantially higher cationic tellurium content present dissolved in the reaction medium which thereby exhibits a substantially improved reaction rate.

FIG. 3 shows tht as the soluble cationic tellurium content of the reaction medium increases the selectivity to useful products also increases. Again, merely operating at high feed total tellurium rate is insufficient. The reaction process of the present invention facilitates the maintenance of higher than otherwise possible concentrations of dissolved cationic material and hence enables attainment of higher useful product selectivity as well as improved reaction rate.

The foregoing experimental results were obtained at a nominal temperature of about 160° C. By way of further illustrating the process of the present invention, the procedures described above were repeated at a nominal reaction temperature of about 140° C. Operations were established so as to maintain an oxygen vent partial pressure of about 27 psi.

When the soluble tellurium content of the reaction medium was maintained at about 1.2 wt. %, the reaction rate observed was about 1.2 g-mols/liter-hr. at a selectivity to useful products of about 90%. The reaction conditions were maintained but the tellurium feed rate was adjusted so as to reduce its dissolved cationic content in the reaction medium to about 0.8 wt. %.

At this latter condition it was observed that the reaction rate dropped to about 1.0 g-mol/liter-hr. at a selectivity to useful products of about 87%.

In Example 1, the gas and liquid feeds are in the relative relationship shown in the drawing, i.e., the recirculating or recycle gas (containing the ethylene being fed) and the fresh molecular oxygen-containing gas are introduced into the oxidation zone separately, with the oxygen-containing gas being introduced into the elongated oxidation zone above the point of introduction of the recycle gas and the recycle gas being introduced above the point of return of the recirculating liquid and the point of introduction of the liquid feed.

When, however, the procedure of Example 1 is repeated, but the oxygen is introduced at a point below the point of introduction of the ethylene-containing recycle gas, but above the point of introduction of the liquid feeds, the reaction selectivity is substantially reduced and acetic acid is oxidized.

Similarly, when the liquid feed and all the liquids are introduced above the points of introduction of both the recycle gas (and ethylene) and the oxygen, even though these two gaseous streams are added in the relative relationships shown in the drawing, the reaction rate and selectivity are again substantially reduced.

In like manner, when the liquid streams are introduced between the two gaseous streams, even though the gaseous streams are in the relative relationship shown in the drawing, poor rate and substantially reduced selectivity result.

As previously mentioned, the process of this invention has been illustrated above in terms of acetic acid and ethylene but it is equally applicable to other carboxylic acids and olefins. Thus, when Example 1 above is repeated employing an equimolar amount of propionic acid in lieu of acetic acid, essentially comparable results are obtained. Production of ethylene glycol propionates, both in terms of rate of formation and yield are comparable to those observed in Example 1 above.

In like manner, when Example 1 above is repeated employing an equimolar amount of propylene in lieu of ethylene as the reactant, essentially comparable results are obtained.

What is claimed is:

1. In a continuous process for the preparation of glycol esters wherein an olefin, a carboxylic acid, and molecular oxygen are reacted in the presence of a catalyst system comprising a variable valent cation and bromine, chlorine, a bromine-containing compound or a chlorine-containing compound, in an oxidation zone containing a body of liquid reaction medium comprising the carboxylic acid and liquid reaction products including said glycol esters and in which the variable valent cation exists during the reaction both in an insoluble form and in a soluble active form, the improvement which comprises employing an oxidation zone which is vertically elongated and has a vertical dimension which is at least 3 times and not greater than 40 times its traverse dimension, continuously withdrawing some of said reaction medium from the upper part of said body and returning at least some of said withdrawn reaction medium to the bottom part of said body in said reaction zone, while continuously introducing olefin, carboxylic acid, recycled unreacted gas and molecular oxygen into the lower part of said body to combine to impart to said reaction medium in said oxidation zone an upward, superficial velocity of at least 0.05 ft./sec., said recycle gas and molecular oxygen being introduced separately into said lower part of said body with the oxygen being introduced at a point above the point of introduction of the recycle gas, and the point of introduction of the recycle gas being above the point of introduction of said withdrawn reaction medium, whereby said insoluble form of said catalyst is continuously converted to the active soluble form to be available in the area of interaction among said oxygen, said olefin and said carboxylic acid to be effective to produce said glycol esters at a high rate and with high selectivity.

2. A process as defined in claim 1, wherein the olefin is ethylene.

3. A process as defined in claim 1, wherein the carboxylic acid is acetic acid.

4. A process as defined in claim 1, wherein the variable valent cation is tellurium cation.

5. A process as defined in claim 1, wherein the upward, superficial velocity is in the range of 0.05 ft./sec. up to about 2 ft./sec.

6. A process as defined in claim 1, wherein the upward, superficial velocity is in the range of 0.1–1.5 ft./sec.

7. A process as defined in claim 1, wherein the olefin is ethylene, the carboxylic acid is acetic acid, the variable valent cation is tellurium cation and the upward, superficial velocity is in the range of 0.05 ft./sec. up to about 2 ft./sec.

* * * * *